United States Patent [19]

Reynolds

[11] Patent Number: 4,490,022
[45] Date of Patent: Dec. 25, 1984

[54] APPARATUS FOR CORNEAL CORRECTIVE TECHNIQUES

[76] Inventor: Alvin E. Reynolds, 7732 E. 105 St., Tulsa, Okla. 74133

[21] Appl. No.: 336,920

[22] Filed: Jan. 4, 1982

[51] Int. Cl.³ .............................................. A61B 3/10
[52] U.S. Cl. .................................... 351/211; 351/212
[58] Field of Search ...................... 351/211, 212, 237; 128/305; 356/392, 393

[56] References Cited

U.S. PATENT DOCUMENTS 4,157,859  6/1979  Terry .................................. 351/212
4,283,124  8/1981  Matsumura ......................... 351/211

Primary Examiner—John K. Corbin
Assistant Examiner—Paul M. Dzierzynski
Attorney, Agent, or Firm—Head, Johnson & Stevenson

[57] ABSTRACT

A quantitative corneascope for use with a surgical microscope in performing corrective techniques on the eye includes a pair of hinged image projection housing members movably mounted on each side of a surgical microscope and a light and image source for reflecting partial segments of placido rings (mires) from the corneal surface of the eye. The microscope utilizes a beam splitter to provide multiple viewing by an operating doctor, an assistant and a television camera. The camera permits viewing of the mires as reflected from the eye, on a monitor. The monitor is provided with apparatus for generating cursor lines on the viewing surface, which cursor lines represent predetermined radii of curvature corresponding to the range of spherical eye shapes. The cursor lines may be adjusted to discrete values in this range of radii of curvature which in turn changes the spacing between the straight lines of the cursor display. The cursor lines may also be adjusted along the X-Y coordinates of the viewing surface.

14 Claims, 3 Drawing Figures

APPARATUS FOR CORNEAL CORRECTIVE TECHNIQUES

BACKGROUND OF THE INVENTION

This invention relates to a method and apparatus for performing corrective techniques on the eye and more particularly to a system, for use with a surgical microscope, for viewing the eye while performing corrective techniques and at the same time displaying comparative images of indicia related to the present shape of the eye and a predetermined eye shape.

Present systems for viewing the eye during surgical techniques involve the use of a surgical microscope for real time viewing and usually, intermittent keratometer measurements before, during and after surgery. This procedure is not only slow and thus time consuming, its accuracy is minimal in that equipment must be moved into and out of the surgical field with each usage. In additional this procedure must take into account the sterile atmosphere of the surgical location and the constant interfacing of measuring equipment with the sterile field. Such a surgical technique might typically follow the pattern of preoperative quantitative keratometer measurement is made to determine what effect the operative procedure has had on the eye. Next suturing is often performed to close incisions in the eye and post-operative keratometer readings are taken to determine the condition of the sutured eye. Each keratometer reading involves the replacement of instrumentation within the surgical field and in precise position with respect to the eye. The preciseness of repositioning of such instrumentation will of course have an effect on the quantitive accuracy of the comparative readings. Additionally present keratometers measure approximately only a 3 mm chord across the center of the eye. The corrective technique of concern in this application more often deals with distortions on the corneal surface between the 2 to 12 mm chords.

An improvement on the above described technique is suggested by mounting a quantitative keratometer on a surgical microscope. The Troutman keratometer exemplifies this manner of treating the problem. The Troutman device is described at pages 28 to 32 of *Microsurgery of the Anterior Segment of the Eye Vol. II*, C. V. Mosby Company, 1977. The Troutman keratometer is characterized by a twelve point light source mounted in a ring about the microscope body. Light is projected to twelve points on the cornea. A keratometer reticle is fitted to the eye piece for the surgeons nondominant eye. It has two concentric circles for reference to the keratometer projection, and split cross hairs to align sutures and mark an astigmatic axis. The Troutman keratometer is a qualitative measuring instrument with a function very different from that of a keratoscope, which is designed for measuring corneal topography. The Troutman keratometer on the other hand is designed specifically to aid the surgeon in the interpretation and correction of meridianal corneal errors. It approximates the powers of astigmatic bands by offering a comparison of reticle circles to an oval reflection of the projected light ring. Interpretation of the projection is a qualitative matter depending on the experience of the surgeon. Keratometer mire patterns are so distorted in the early postoperative course as to be of little value in making determinations concerning refraction. Thus, no present technique or system is available to facilitate accurate determination of corneal topography in a real time intraoperative situation. Also lacking is a system offering a conveniently usable comparison of real time intrasurgical data with cursor indicia indicative of a predetermined or preoperative condition.

It is therefore an object of the present invention to provide a new and improved method and apparatus for providing simultaneously on a convenient viewing surface, real time quantitative data relating to the present corneal topography, and predetermined data relating to a preoperative condition or desired corneal surface condition, with such system being arranged for use intraoperatively in conjunction with a surgical microscope.

SUMMARY OF THE INVENTION

With this and other objects in view the present invention contemplates a quantitative keratoscope system for use with a surgical microscope in performing corrective techniques on the eye. Partial segments to placido rings are reflected off of the eye in a meridianal pattern of mires. Cursor lines are capable of being generated and projected simultaneously on a viewing surface, with such cursor lines corresponding to known or predetermined radii of curvature of a spherical surface, these cursor lines may be moved laterally with respect to one another to vary their pattern in accordance with an infinite variety of radii of curvature within the range of corneal curvatures. The group of cursor lines may be moved along the X-Y coordinates of the viewing surface to bring them into coincidence with a real time image of the indicia representing the present corneal topographic condition. The mires may be observed on the corneal surface by the operating physician and assistants as well as be projected onto a separate viewing surface. The equipment for reflecting mires from the corneal surface may be conveniently moved to a stowed position to allow more freedom of movement in the surgical field, and then returned to its operative position without changing the positional relationship of the keratoscope, microscope, and object corneal surface. A focusing mark on the viewing surface and in the microscope image provides a check of this positional relationship.

Another aspect of this invention relates to a surgical technique whereby a preoperative quantitative kerstoscope reading is taken with the surgical microscope in its operative position. The preoperative image of mires on the corneal surface may be recorded by bringing the cursors into coincidence with the mires and reading out digitally on the viewing surface an indication of the radius of curvacture corresponding to the mires. The housing for projecting the mire to be reflected from the corneal surface may then be moved to a stowed position within the surgical field but out of the surgeons way to permit freedom of movement within the surgical field during the operation. At any time during the operation, such as during suturing, the mires projection housing may be returned to its exact same position in the surgical field for providing a real time image of mires on the present corneal surfaces. Cursor lines or other indicia corresponding to the preoperation corneal conditions may then be superimposed on the viewing surface to provide an indication of the preoperative curvature of the corneal surface. A comparison of the preoperative curvature with the present condition permits adjustment of the sutures until the preoperative condition or an otherwise desired condition is attained, whereupon the sutures are fixed.

In still another aspect of the invention, the relative position of real time mires and predetermined or desired cursor lines can be used to compute a refractively corrected corneal surface configuration, and read out such computation. The cursor lines may then be set to correspond to such computed configuration. A ring is then implanted in the corneal surface with its diameter being adjusted until the real time image and computed image are in coincidence, at which time the ring diameter is fixed.

In yet another aspect of the invention, the meridianal orientation of the projected mires may be conveniently moved in a horizontally arcuate path to incrementally provide full viewing coverage of the corneal surface.

DESCRIPTION OF THE PREFERRED EMBODIMENT

Figure 1:
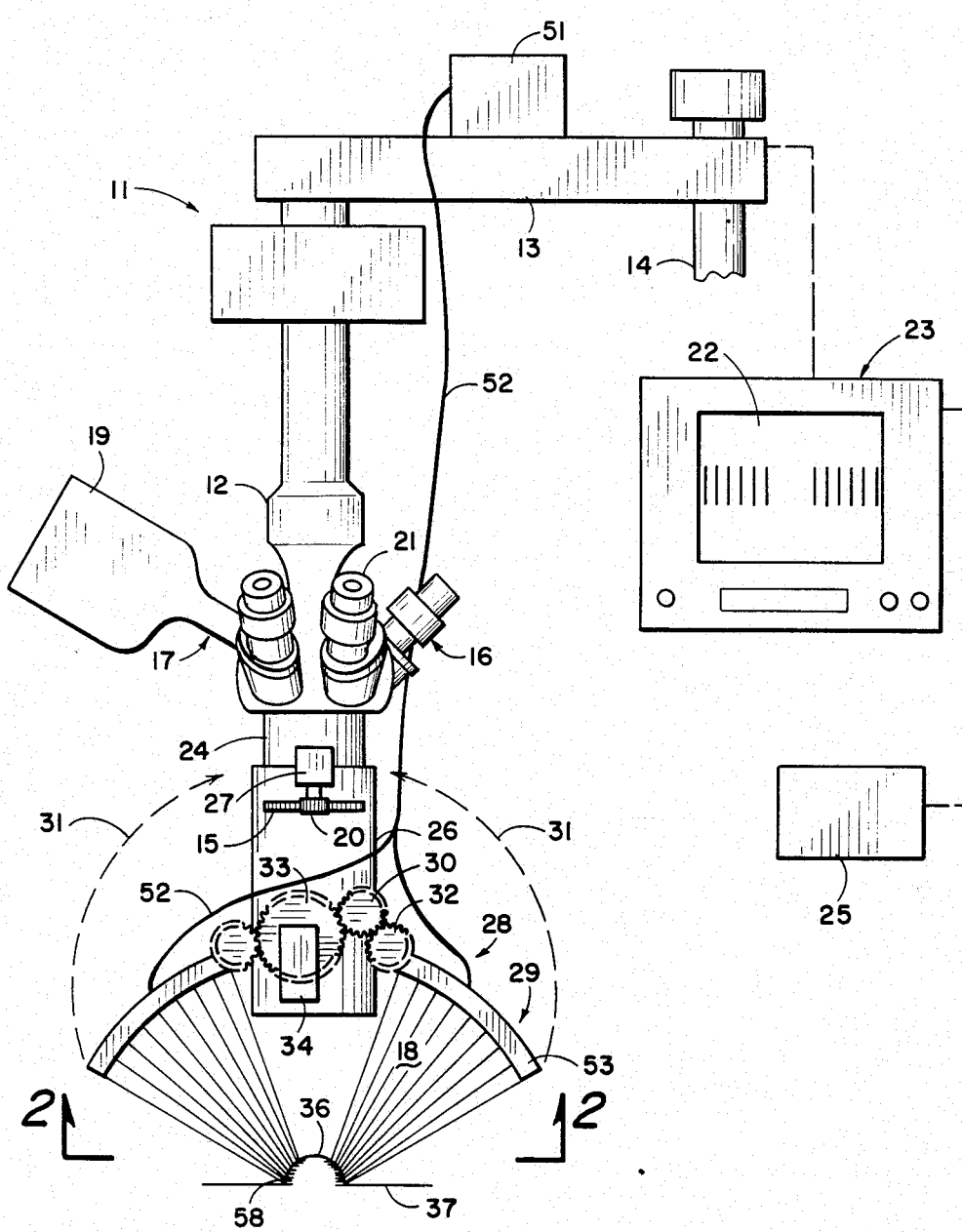
FIG. 1 is an elevational schematic view of a quantitative keratometer and corneascope mounted on a surgical microscope.

Referring first to FIG. 1 of the drawings, a surgical microscope 11 is shown having a main body portion 12 movably suspended from an arm 13, the arm is movably supported on the stand 14 (partially shown) which has provisions (not shown) for positioning the microscope by means of foot operated switches. This arrangement eliminates the need for persons working in the sterile surgical field to touch the microscope, at least a portion of which, is outside the sterile field. On the body 12 of the microscope are a plurality of viewing positions radially arranged about the body 12 and equipped with (in the present case) two operator viewing positions 16, and one video camera position 17. The operator positions 16 are provided with binocular eye pieces 21 to permit the surgeons viewing of the surgical field 18 beneath the microscope. TV camera 19 provides means for projecting the image viewed by the surgeon and/or assistants onto a remote viewing surface 22 mounted on a monitor 23. The monitor 23 is also provided with computer and signal generating means 25.

The body 12 of the microscope has a lower body portion 24 extending downwardly below the viewing positions 16 and camera position 17. The lower housing portion 24 includes the main optical system of the microscope. Arranged on the lower body portion 24 of the standard surgical microscope is a sleeve 26 which is mounted for rotational movement with respect to lower body portion 24. A motor unit 27 is arranged to drive the sleeve 26 in a rotational path about the lower portion 24. The motor unit 27 is mounted on lower housing portion 24 and has a gear 20 driven by the motor 27. The gear cooperatively engages an arcuate rack 15 on the outer peripheral surface of the sleeve 26. When the motor 27 is driven, the sleeve 26 is caused to rotate on body portion 24. A foot operated switch may be connected by suitable wiring means to permit operation of the motor unit 27.

A projection assembly 28 is mounted on the lower end of sleeve 26 and includes a pair of projection housing members 29 which are mounted for pivotal movement with respect to the sleeve 26 from an operative position as shown in FIG. 1 along a path shown by the dotted lines and arrows 31 to a stowed position against the lower body portion 24. Driven gears 32 connected to the housing member 29 are arranged to cooperatively engage a driving gear 33 and idler 30, mounted on the sleeve 26. A motor 34, also mounted on the sleeve 26 rotates the gears and idler, in response to a foot operated control device (not shown), to cause the housing members 29 to move between the operative and stowed positions described above. FIG. 1 also shows a spherical surface viewing object 36 positioned on a fixed surface 37 within the surgical field. A light source 51 is shown positioned on top of arm 13 of the surgical microscope. The light source can also be a source of light within the housing members 29 or, as shown in FIG. 1, can be remote to the housing 21 and utilize fiber optic bundle 52 to transmit light from the source 51 to the interior of the housing members 29.

Figure 2:
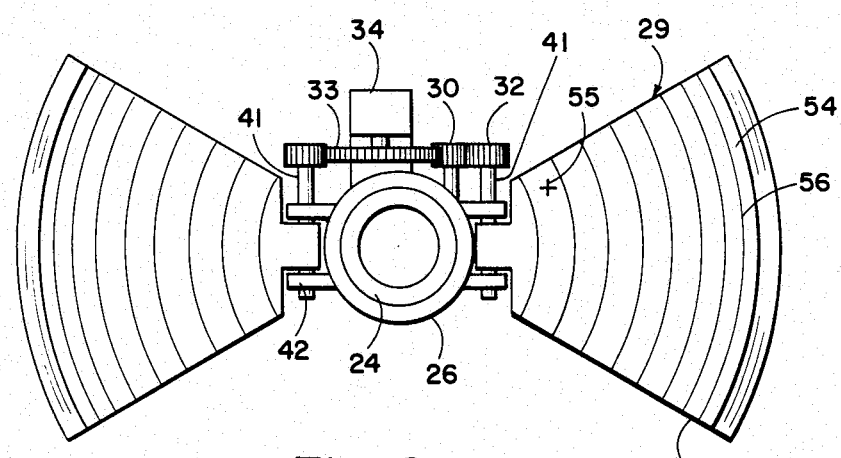
FIG. 2 is a bottom view of a portion of the apparatus of FIG. 1 taken along line 2—2 of FIG. 1.

FIG. 2 shows the bottom side of the housing members 29 and their cooperative relationship with the lower portion 24 of the microscope body 12. The gears 32 are connected to axle pins 41. Pins 41 are rotatably mounted within bearing arms 42 which in turn are connected to the sleeve 26. Pins 41 are formed on or are connected to the inner ends of housing member 29 and thus the housing members 29 are caused to rotate with the pins 41 and gears 32. The radially angular configuration of the side walls 53 of the housing members 29 describe approximately a sixty degree segment of a circle. Between the side walls 53 the lower surface 54 of the housing members is constructed of a translucent material such as Lucite, which is covered with an opaque material such as black paint. Evenly spaced arcuate lines 56 are inscribed into the painted surface 54 to leave a translucent surface beneath the lines 56. Thus the light delivered by the fiber optics bundle 52 or other light source to the interior of housing 29 is permitted to emanate through the lines 56. This in turn causes the projection of an arcuate pattern of light lines 58 (mires) which are reflected from the spherical surface 36. Also inscribed into the opaque surface 54 is a cross mark 55 which permits focusing of the mires on the viewing surface.

Figure 3:
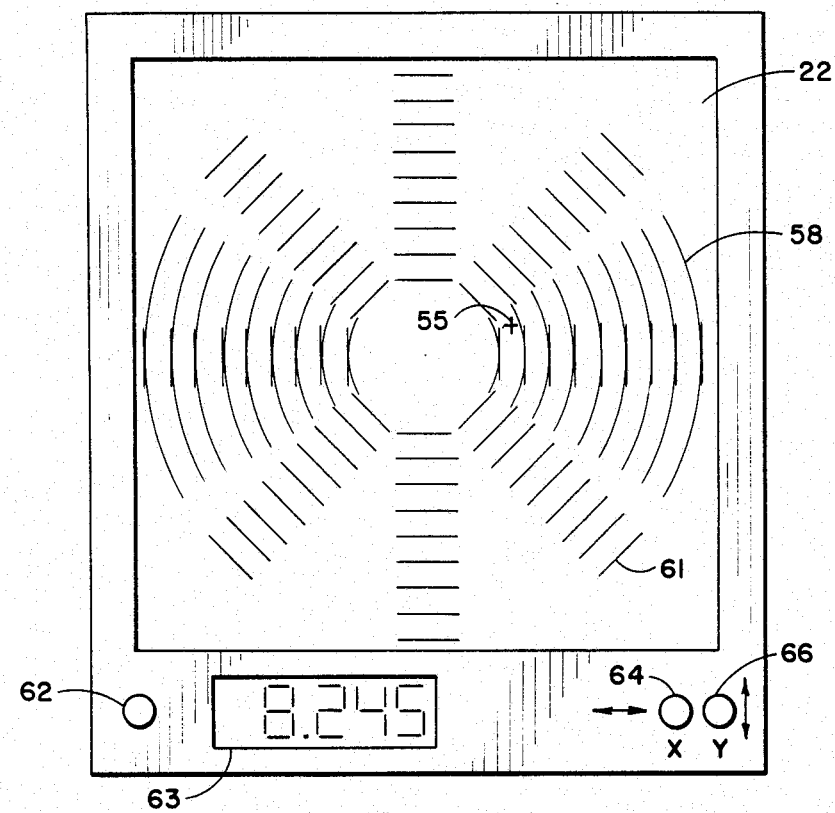
FIG. 3 is a schematic view of a viewing surface for projecting data from the keratometer and corneascope, and showing indicia representing predetermined generated data for comparison with the real time data from the surgical corneascope and keratometer.

Referring now to FIG. 3 of the drawings, the monitor 23 is shown having a viewing surface 22 with indicia displayed thereon. The image of the mires 58 and cross mark 55 reflected from the spherical surface 36 is detected by the video camera 19 and transmitted to the viewing surface 22 by well known video transmission techniques. It is appreciated that any of the sequential images making up the video transmission can be recorded and stored for later reference. This may be done on video tape as well as by other more precise electronic data storage techniques. Such a stored image may be later projected onto the viewing surface either alone or compositely with another image such as a real time image. The cross mark 55 is also projected onto the viewing surface 22 to permit monitoring of the equipment focus on the surface 22. The computation and signal generating means 25 is comprised of electronic components, not described in detail here, for generating a pattern of straight lines or cursors 61 for projection onto the viewing surface 22. These lines may be arranged in various maridianal patterns such as the horizontal display depicted in FIG. 1 or in any one of various maridinal courses shown in FIG. 2. By means of computing components in the signal generator 25, these cursor lines may be varied in their spacing from one another to correspond to various radii of curvature of a spherical surface as projected onto the viewing surface 22 from a spherical object 36 on surface 37. For example, in order to calibrate the accuracy of the cursor image 61, a spherical ball of known diameter is placed on the surface 37. Light from source 51 is reflected from the surface 36 as mires 58 which in turn are displayed on the viewing surface 22. The cursor lines which may be moved relative to one another on the viewing surface 22 are moved by means of a radius of curvature adjustment control knob 62 until they are in alignment with the mires reflected from the object of known diameter. A digital readout 63 displays a value of the cursors for that discrete separation of lines. The readout number should correspond exactly with the known diameter of the sphere 36. If the reading is out of correspondence, an adjustment is made electronically in the signal generator and computation unit 25 to bring the read out into coincidence with the known dimension of the spherical surface 36. Control knobs 64 and 66 on the monitor 23 permit the entire field of cursors to be adjusted along X and Y coordinates respectively. This permits precise overlaying of the generated cursors 61 with the reflected mires 58 for comparing a known spherical dimension with the real time dimension shown by the mires.

FIG. 3 shows the mires being projected onto surface 22 in oppositely occuring sixty degree arcuate segments formed along a horizontal meridian. The motor 27 (FIG. 1) and rotatably arranged sleeve 26 provide a means for rotatably moving the projection members 29 in either direction in a horizontal plane as viewed in FIG. 1. Thus by moving the member 29 sixty degrees in both directions from that shown, the entire surface of the spherical object 36 may be scanned by the mires. This arrangement of segmented movable projection members permits the apparatus to be operated over a surgical field without impairing movement of the surgeon and assistants within the field and yet still offering the advantages afforded by the quantitative keratoscope projections.

The system described above may be used to perform keratoplasty and keratorefractive techniques for example, as follows: In a cataract operation, commonly the cataracts are removed successfully from the eye, however, refractive errors are induced as a result of asymmetry stemming from suture involvement in the cornea. The cataract incision may be tied too tightly at the time of surgery, producing with-the-rule astigmatism; or too loosely, producing wound gape thus flattening of the superior cornea and against-the-rule astigmatism. The above described keratoscope easily differentiates the localization of the suture defect in these two situations and permits quantitative correction to reform the error. A procedure that can be followed in such an operation might comprise reflecting mires 58 from the preoperative corneal surface, and projecting an image of the mires so reflected onto the viewing surface 22. The cursors 61 are then brought into coincidence with the mires reflected from the preoperative corneal surface. A digital reading of this discrete radius of curvature can then be read out on the display 63. Alternatively the preoperative mires image may be stored for later viewing. The cataract operation is then performed. Before sutures are tightened, the keratoscope is again focused on the postoperative corneal surface. The cursors are set to the preoperative discrete valve or the preoperative mire image is displayed, whereupon the sutures may be manipulated to bring the postoperative corneal surface into conformity with the preoperative corneal shape. It is readily seen that modifications and variations on this and other surgical techniques can be arranged and still fall within the spirit and scope of the system described.

A keratorefractive procedure which readily lends itself to this system is described in applicant's co-pending application entitled "Method and Apparatus for Corneal Curvature Adjustment" and filed of even date herewith. This keratorefractive technique briefly involves determining the desired shape of a corneal surface for correcting the refractive error of a specific corneal surface. A plastic ring is then inserted into the corneal stroma, such plastic ring being split at one point to provide two ends open for relative movement to one another. After inserting the ring, the above described keratoscope is positioned over the eye whereupon the mires reflected from the eye are projected onto the viewing surface 22. The control knob 62 is then turned until the desired numerical value of corneal curvature is displayed at 63. This then places the cursors at the desired separation to correspond to a correct corneal topography. The plastic ring is then adjusted in diameter within the corneal stroma to bring the mires into coincidence with the cursors, whereupon, the ends of the ring are fixed relative to one another to provide a corrected corneal surface.

The apparatus described herein can be used simply as a quantitative keratometer by placing the cursor marks into coincidence with the reflected mires and then read out the radius of curvature. In fact, any number of variations of techniques may be thought of for utilizing the system described above, as well as modifications to the system specifically described. For example, one can display two sets of mires, one being real time and another, a stored image. These can then be superimposed or otherwise compared, for example, by using cursors, to facilitate eye correction.

Therefore, while particular embodiments of he present invention have been shown and described it is apparent that changes and modifications may be made without departing from this invention in its broader aspects, and therefore, the aim in the appended claims is to cover all such changes and modifications as fall within the true spirit and scope of the invention.

What is claimed is:

1. Apparatus for use with a surgical microscope to perform corrective techniques on the eye, comprising:
   means for projecting indicia onto the eye, a reflected image therefrom being indicative of corneal topography, said image being viewable through a surgical microscope, said means for projecting indicia is comprised of a pair of projecting members extending outward and downwardly from the sides of the surgical microscope and hingedly fixed to the surgical microscope and further including means for moving said projecting members between an operative, extended position and a stored position against the body of the microscope;
   means or displaying on a viewing surface an image related to a predetermined surface shape; and
   means or superimposing the indicia indicative of corneal topography onto the viewing surface with the image related to the predetermined shape to permit comparison of the indicia and image.

2. The apparatus of claim 1 and further including means for recording information indicative of the image related to a predetermined surface shape.

3. The apparatus of claim 1 and further including means for adjusting the image related to a predetermined surface shape to conform to a variety of predetermined shapes.

4. The apparatus of claim 3 wherein said predetermined shapes are spherical in nature and further including means for displaying a number indicative of the radius of curvature of said predetermined shapes.

5. The apparatus of claim 4 wherein said means for adjusting comprises means for adjusting the radius of curvature of the spherical shapes through an infinite range of sizes.

6. The apparatus of claim 1 and further including means for adjusting said image along vertical and horizontal coordinates in the viewing plane.

7. The apparatus of claim 1 and further including means for mounting said projecting members for rotational movement within a plane perpendicular to the viewing axis of the microscope.

8. The apparatus of claim 1 wherein said projecting means includes means for selectively moving said projecting means into and away from the area in which the corrective technique is being performed.

9. Apparatus for use with a surgical microscope for performing corrective techniques on the eye, comprising:

means movably mounted about the body of the surgical microscope for projecting indicia comprised of partial segments of placido rings onto the surface of the eye; and means for viewing the eye through the microscope to permit corrective techniques to be performed on the eye while the apparatus is in place over the eye, means to pivot said indicia projecting means from an outwardly projecting operative position adjacent the bottom of said microscope to a stowed position above said bottom and alongside the microscope body to permit freedom of movement below said bottom by a person performing corrective techniques on the eye.

10. The apparatus of claim 9 and further including a viewing surface and means for detecting an image of the projected indicia on the eye and for displaying the detected image on the viewing surface.

11. The apparatus of claim 10 and further including means for displaying predetermined indicia on the viewing surface, such predetermined indicia being indicative of a known corneal shape.

12. The apparatus of claim 11 and further including means for moving the predetermined indicia along horizontal and vertical coordinates on the viewing surface.

13. The apparatus of claim 9 and further including means for rotatably moving said projecting means in a plane perpendicular to the viewing axis of the microscope.

14. The apparatus of claim 11 and further including means for conveniently changing the predetermined indicia to correspond to an infinite range of corneal shapes; and means for reading out a numerical value indicative of a parameter of the corneal shape.

* * * * *